United States Patent [19]

Smith et al.

[11] Patent Number: 4,530,828
[45] Date of Patent: Jul. 23, 1985

[54] NAIL CONDITIONER

[75] Inventors: Walter P. Smith, Scudy Hook; Sergio Nacht, Weston, both of Conn.

[73] Assignee: Richardson-Vicks Inc., Wilton, Conn.

[21] Appl. No.: 419,023

[22] Filed: Sep. 16, 1982

[51] Int. Cl.³ .............. A61K 7/04; A61K 31/00; A61K 47/00; A61K 7/06
[52] U.S. Cl. .............................. 424/61; 424/70; 514/774; 514/552; 514/558; 514/553; 514/2
[58] Field of Search .............. 424/61, 70, 168, 171, 424/172, 177, 359

[56] References Cited

U.S. PATENT DOCUMENTS

| 3,907,580 | 3/1973 | van Ham | 424/61 |
| 4,070,451 | 11/1976 | Price | 424/61 |
| 4,115,313 | 2/1976 | Lyon et al. | 424/61 |
| 4,402,935 | 9/1983 | Gordon et al. | 424/61 |

FOREIGN PATENT DOCUMENTS 1603765 7/1971 France ..................... 424/61

OTHER PUBLICATIONS

Balsam et al., Cosmetics: Science and Technology, vol. 2, pp. 564–571, 2nd ed., Wiley, New York.

*Primary Examiner*—Sidney Marantz
*Assistant Examiner*—Shawn P. Foley
*Attorney, Agent, or Firm*—Salvatore R. Conte

[57] ABSTRACT

A nail conditioning composition comprising an aqueous emulsion of sodium lauryl sulfate, urea and hydrolyzed animal protein in the aqueous phase and mineral oil, cholesterol and a lipid in the oil phase, said lipid being cetyl alcohol, cetyl palmitate or a base salt of palmitic or stearic acids. The composition moisturizes and imparts flexibility to the nail and softens the cuticle area.

7 Claims, No Drawings

4,530,828

NAIL CONDITIONER

BACKGROUND OF THE INVENTION

This invention relates to compositions for the treatment of keratinous tissues, such as human fingernails and toenails, and for softening cuticles. It is particularly concerned with the provision of an improved composition for treating and maintaining nails in a supple, healthy condition. The human nail comprises structural protein, or scleroprotein, which is hard and insoluble and is made up of keratine. In addition to its inherent hardness, the human nail often becomes dry and brittle and subject to breaking, cracking or splitting. A nail conditioning composition which substantially overcomes such cosmetic problems is herewith provided.

SUMMARY OF THE INVENTION

This invention relates to an improved composition for the treatment of human nails and similar keratinous tissues. When applied topically to nails, the subject composition provides a markedly superior hydrating effect which maintains the nails in a softened condition for a substantial duration of time.

According to the invention, such improved nail conditioning composition is an aqueous emulsion comprising six essential active ingredients. The composition comprises sodium lauryl sulfate, urea and hydrolyzed animal protein as three essential active ingredients in the aqueous phase and mineral oil, cholesterol and a lipid component as three essential active ingredients in the oil phase, said lipid component being selected from the group consisting of cetyl alcohol, cetyl palmitate and a base salt of a fatty acid such as palmitic acid or stearic acid, and mixtures thereof.

Said actives provide a formulation that is unexpectedly and markedly superior with regard to softening nails than presently available commercial preparations. The actives presumably cooperate in binding to nail protein and to water, thereby hydrating and conditioning the nail.

In addition to the aforementioned active ingredients, other additives may be advantageously employed in the subject compositions such as, for example, thickening agents, preservatives, alkali for pH adjustment, surfactants, emollients, colorants, odorants and the like. One optional ingredient found particularly suitable for use in conjunction with, but not in lieu of, sodium lauryl sulfate is the non-ionic surfactant, octylphenoxy polyethoxyethanol, also known as octoxynol 9 or Triton X-100 (trade name of Rphm & Haas).

PRIOR ART

U.S. Pat. No. 4,070,451 describes an aqueous emulsion composition for softening keratinous tissues, in particular, animal hooves, which composition contains, among others, certain essential ingredients as are employed in the subject composition, for example, sodium lauryl sulfate, mineral oil and, in differing amount, hydrolyzed animal protein. However, whereas said prior art composition requires ten essential ingredients other than water, the subject composition requires only six. Other differences are also evident, e.g., in percentage ranges, lipid makeup, etc. Furthermore, as shown hereinafter, the subject composition is markedly superior to such prior art composition, the former maintaining the nails in a softened condition for a much longer period of time.

DESCRIPTION OF THE PREFERRED EMBODIMENTS

As set forth above, the composition of the invention comprises an aqueous emulsion containing the ingredients tabulated below. Said ingredients are essential for accomplishing the desired results and are present in percent by weight, based on the weight of the total composition, within the following ranges:

| Ingredients | % w/w |
| --- | --- |
| Hydrolyzed animal protein | 0.6–10.0 |
| Urea | 0.6–10.0 |
| Sodium lauryl sulfate | 0.06–2.5 |
| Mineral Oil | 2.0–7.8 |
| Cholesterol | 0.8–1.2 |
| Lipid | 4.5–7.3 | wherein said lipid is a member selected from the group consisting of cetyl alcohol, cetyl palmitate, and a base salt of a fatty acid and mixtures thereof, said fatty acid being selected from the group consisting of palmitic acid, stearic acid and mixtures thereof.

Of these ingredients, the first three are contained in the aqueous or water phase of the emulsion and the latter three basically consititute the oil phase of the emulsion. In general, the aqueous phase to oil phase ratio is, respectively, from about 2:1 to about 10:1 parts, and preferably from about 5:1 to about 8:1 parts, by weight.

Without being bound thereby, it is believed that the actives in the water phase allow product water or endogenous water to be retained by fingernails and the like while the occlusiveness and emollient effect of the oil phase helps prevent such water from escaping, thereby maintaining the nails in a hydrated and supple state. This nail hydrating capability of the subject compositions avoids brittleness and a dried-out condition leading to cosmetically undesirable nail cracking, chipping, splitting and the like. The subject compositions also have a cosmetically desirable non-greasy "feel" on skin and substantial lack of skin friction which, together with the hydrating effect, provides a desirable product for softening cuticles and hardened skin.

It has been observed that the indicated aqueous phase alone does not produce a long-lasting softening effect on nails and that the indicated oil phase is essential for efficacy. All three ingredients of the oil phase within the respective indicated ranges, namely, mineral oil (light or heavy), cholesterol and the lipid component are required for optimal efficacy. As the lipid component, any one of the three indicated entities may be advantageously utilized, namely, cetyl alcohol, cetyl palmitate or the fatty acid base salt. However, a mixture of all three is preferred, most preferably in a ratio of about 1:1:1 by weight.

As the lipid component, a base salt of the fatty acids, palmitic acid and stearic acid, may be employed. Typical of such salts are the ammonium, alkali metal (sodium and potassium preferred) and alkaline earth metal palmitates and stearates, as well as organo amino salts of said acids, e.g., mono-, di- and trialkylamino, mono-. di- and trialkanolamino (triethanolamino preferred), and the like, palmitates and stearates. Such base salts may be preformed and included as such in the instant compositions or may be formed in situ by reaction of the fatty acid with an equivalent amount of the appropriate base, for example, ammonium hydroxide, sodium hydroxide, magnesium hydroxide, triethanolamine, and the like.

The indicated combination of active ingredients in the aqueous phase within the respective indicated ranges is also essential, namely hydrolyzed animal protein, urea and sodium lauryl sulfate. Typically suitabale hydrolyzed animal proteins are, for example, soluble collagen (preferred), such being commercially available from Vevy Laboratories under the trade name "Collagenon," a keratin polypeptide commercially available from Croda Inc. under the trade name "Crotein WKP," and the like. The sodium lauryl sulfate serves primarily as the surfactant in the formation of the emulsified composition. When the % w/w concentration of one or more of these three essential actives is below the indicated minimum, the nail softening efficacy of the relative product is observed to be markedly inferior both in duration and magnitude of softening.

Advantageously, the subject compositions may include th following ingredients within the specified ranges, based on the total weight of the compositions:
A. in the water phase:
(i) a thickener or gelling agent, about 0.1–0.5% w/w such as, for example, sodium carboxymethylcellulose, the preferred synthetic gel-forming material commercially available from the B. F. Goodrich Chemical Co. under the trade name "Carbopol 934," and the like, it being noted that the addition of an alkali metal (preferably sodium) or ammonium hydroxide is recommended to aid solubilization of said Carbopol 934 and to increase its viscosity;
(ii) a water-soluble preservative, about 0.05–0.3% w/w, such as, for example, benzoic acid, the preferred imidazolinidyl urea, and the like.
(iii) a non-ionic surfactant to aid emulsification of the composition, about 0.5–5.0% w/w, such as, for example, the preferred octylphenoxy polyethoxyethanol; and
(iv) sufficient alkali, e.g., an alkali metal (sodium preferred) or ammonium hydroxide to adjust the pH if so needed to the preferred pH of about 7.1–7.6; and
B. in the oil phase:
(i) an oil-soluble preservative to prevent bacterial spoilage about 0.05–0.3% w/w, such as for example, one or more lower alkyl (1–4 Cs) p-hydroxybenzoates, e.g., methyl and propyl paraben; and
(ii) an emollient, about 0.5–5.0% w/w, such as, for example, a natural oil, e.g., olive oil, sunflower oil, peanut oil, corn oil and the like, or a lanolin derivative, e.g., lanolin oil, lanolin wax, lanolin alcohol and the like, or mixtures thereof.

Additional optional ingredients may be utilized so long as they are chemically and esthetically compatible with the remainder of the composition, for example, a colorant, e.g., FD&C Blue #1, FD&C Yellow #5, FD&C Red #40 and the like, which is soluble in the aqueous phase and which is employed as an aqueous solution of suitable dilute concentration; and an odorant such as any suitable perfume oil, whether naturally derived or synthetically prepared, or blends thereof, and which is generally incorporated into the composition at a temperature such as to minimize loss of the volatile essences.

Formulations of this invention include lotions and creams, which formulations are readily obtainable by standard cosmetic manufacturing techniques such as by varying the % w/w concentrations of the indicated components within the specified ranges. For example, by decreasing the surfactant content, i.e., either sodium lauryl sulfate alone or in conjunction with a non-ionic surfactant, or by increasing the mineral oil content, or by maximizing the content of gelling agent, a corresponding increase in viscosity of the end product emulsion is obtained, thereby providing consistencies ranging from watery lotions to rich creams.

The subject compositions are desirably produced by separately preparing the oil phase and the water phase and then combining such two phases to form the desired emulsion or cream. Preferably, the coloring and volatile perfuming agents are added after some cooling of the combined phases.

In general, the ingredients of the oil phase, i.e., the mineral oil, cholesterol and lipid, and other oil-soluble additives are mixed together in a suitable heating vessel at ambient temperatures and slowly heated with stirring to a temperature of about 75°–80° C. until solubilization is achieved. In the preparation of the water phase, the water is placed in a separate heating vessel at ambient temperature and the water-soluble ingredients are added, e.g., the hydrolyzed animal protein, urea and sodium lauryl sulfate. The resulting mixture is also slowly heated with stirring to about 75°–80° C. for complete solubilization.

With the oil phase and the water phase both at or about the same top temperature, the heated oil phase is added slowly to the heated water phase with vigorous agitation, for example, using a suitable mechanical stirrer. The resulting mixture is allowed to gradually cool while it is being continuously stirred so that the desired emulsion or cream is formed.

At a temperature of 50° to 60° C., preferably about 55° C., the coloring ingredient (if used) is added, stirring being cntinued. When the emulsion reaches a temperature of 40° to 50° C., the perfume ingredient (if used) is added. Pouring of the final emulsion into suitable containers such as jars, squeezable bottles, and the like, takes place at a temperature of 40° to 44° C., usually around 42° C.

The following examples of the subject compositions illustrate the instant invention. All references to "%" are by weight unless otherwise noted.

| Ingredients | Example No. 1 | Example No. 2 | Example No. 3 | Example No. 4 |
| --- | --- | --- | --- | --- |
| Hydrolized animal protein (soluble collagen) | 5.0% | 1.0% | 5.0% | 5.0% |
| Urea | 5.0 | 1.0 | 5.0 | 5.0 |
| Sodium lauryl sulfate | 0.5 | 0.1 | 0.5 | 0.5 |
| Octylphenoxy polyethoxyethanol | | 1.0 | 2.0 | 1.0 |
| Mineral oil (heavy) | 2.5 | 5.0 | 2.5 | 2.0 |
| Olive oil | | | | 1.0 |
| Lanolin oil | | 2.0 | | 2.0 |
| Cetyl palmitate | | 1.0 | 2.3 | 2.3 |
| Cetyl alcohol | | 2.0 | 2.3 | 2.3 |
| Stearic acid | | 2.5 | | |
| Palmitic acid | 6.9 | | 2.3 | 2.3 |
| Cholesterol | 1.5 | 1.0 | 1.0 | 1.0 |
| Triethanolamine | | 1.5 | | |
| Imidazolinidyl urea | | 0.25 | | |
| Thickener (Carbopol 934) | | 0.2 | | |
| Colorant | | 0.12 | | |
| Odorant | | 0.4 | | |
| Water, q.s. ad | 100.0% | 100.0% | 100.0% | 100.0% |
| pH | 7.1* | 7.6 | 7.1* | 7.1* |
| Consistency | (watery | (rich | (watery | (thick |

| Ingredients | Example | | | |
|---|---|---|---|---|
| | No. 1 | No. 2 | No. 3 | No. 4 |
| | (lotion) | (cream) | (lotion) | (lotion) |

*Adjusted with sodium hydroxide

The instant compositions possess superior nail-conditioning acitivity as indicated by their marked softening effect which lasts over a significant period of time. In general, the maximum softening effect is observed within 10–30 minutes after application and condiserable softening is still maintained after 4–6 hours. For example, in measuring the visco-elastic properties of human nail clippings resulting from a single application of the compositions of Examples 1–4, a rapid 50–60 percent increase in softening is observed with an appreciable softening of at least 20 percent remaining after 5 hours. In contrast, presently available commercial nail treatment formulations, such as, for example, the composition of the aforementioned U.S. Pat. No. 4,070,451 marketed under the trade name "Barielle Nail Strengthener Cream" by Barielle Ltd., rapidly and completely lose their nail softening ability within a short period of time, generally 1–2 hours.

This invention thus provides a markedly advantageous nail conditioning composition which is easily utilizable by single application to the nail surface. Gentle rubbing of the applied composition into the nail (or cuticle) surface is recommended for optimal activity. Furthermore, the subject compositions do not interfere with or deleteriously effect subsequent application of cosmetic preparations such as nail polishes or lacquers.

We claim:

1. A composition for the treatment of human nails or cuticles consisting essentially of an aqueous emulsion containing the following ingredients in percent by weight, based on the weight of the total composition:

| Hydrolyzed animal protein | 0.6–10.0 |
|---|---|
| Urea | 0.6–10.0 |
| Sodium lauryl sulfate | 0.06–2.5 |
| Mineral oil | 2.0–7.8 |
| Cholesterol | 0.8–1.2 |
| Lipid | 4.5–7.3 | wherein said lipid is a member selected from the group consisting of cetyl alcohol, cetyl palmitate, a base salt of a fatty acid and mixtures thereof, said fatty acid being selected from the group consisting of palmitic acid, stearic acid and mixtures thereof, and said base salt being selected from th group consisting of ammonium, alkali metal, alkaline earth metal and alkanolamino.

2. The composition of claim 1 wherein said base salt is a sodium salt.

3. The composition of claim 1 wherein said base salt is a triethanolamine salt.

4. The composition of claim 1 wherein said lipid comprises a mixture of (i) cetyl alcohol, (ii) cetyl palmitate and (iii) a base salt of a fatty acid selected from the group consisting of palmitic acid, stearic acid and mixtures thereof.

5. The composition of claim 4 wherein said mixture of (i), (ii) and (iii) is in a respective weight ratio of about 1:1:1.

6. The composition of claim 1 which further includes from about 0.5 to 5.0% of a non-ionic surfactant.

7. The composition of claim 6 wherein said non-ionic surfactant is octylphenoxy polyethoxyethanol.

* * * * *